(12) United States Patent
Malofsky et al.

(10) Patent No.: US 10,086,355 B2
(45) Date of Patent: *Oct. 2, 2018

(54) METHOD TO OBTAIN METHYLENE MALONATE VIA BIS(HYDROXYMETHYL) MALONATE PATHWAY

(71) Applicant: SIRRUS, INC., Loveland, OH (US)

(72) Inventors: Bernard Miles Malofsky, Bloomfield, CT (US); Adam Gregg Malofsky, Loveland, OH (US); Jeffrey M. Sullivan, Goshen, OH (US); Philip B. Kisanga, Mason, OH (US); John Joseph Anderson, Mount Vernon, IN (US); Michael Charles Milner Cockrem, Madison, WI (US); Philip Jay Carlberg, Loveland, OH (US)

(73) Assignee: Sirrus, Inc., Loveland, OH (US)

( * ) Notice: Subject to any disclaimer, the term of this patent is extended or adjusted under 35 U.S.C. 154(b) by 11 days.

This patent is subject to a terminal disclaimer.

(21) Appl. No.: 15/345,976

(22) Filed: Nov. 8, 2016

(65) Prior Publication Data

US 2017/0050167 A1    Feb. 23, 2017

Related U.S. Application Data

(63) Continuation of application No. 14/823,581, filed on Aug. 11, 2015, now Pat. No. 9,522,381, which is a
(Continued)

(51) Int. Cl.
*B01J 8/06* (2006.01)
*B01J 19/24* (2006.01)
(Continued)

(52) U.S. Cl.
CPC ............ *B01J 19/245* (2013.01); *B01J 8/067* (2013.01); *B01J 29/40* (2013.01); *C07C 67/31* (2013.01);
(Continued)

(58) Field of Classification Search
CPC ......... B01J 8/00; B01J 8/02; B01J 8/06; B01J 8/067; B01J 19/00; B01J 19/24;
(Continued)

(56) References Cited

U.S. PATENT DOCUMENTS 2,212,506 A  8/1940  Bachman
2,245,567 A  6/1941  Brant et al.
(Continued)

FOREIGN PATENT DOCUMENTS

CN    102901754 A     1/2013
DE    19508049 A1    9/1996
(Continued)

OTHER PUBLICATIONS

Second Office Action from the State Intellectual Property Office of the People's Republic of China for Application No. 201480003455.7, dated Sep. 12, 2016.
(Continued)

*Primary Examiner* — Natasha E Young
(74) *Attorney, Agent, or Firm* — Young Basile Hanlon & MacFarlane, P.C.

(57) ABSTRACT

Method to obtain methylene malonate and related monomers following a bis(hydroxymethyl) malonate pathway. A bis(hydroxymethyl) malonate intermediary is subsequently reacted (i.e., subjected to thermolysis) to provide a methylene malonate monomer species. A source of formaldehyde (e.g., formalin) is provided in the presence of a basic catalyst (e.g., calcium hydroxide), to which a malonate (e.g., diethyl malonate) is added under suitable reaction conditions to obtain the desired intermediary (e.g., dialkyl bis(hydroxymethyl) malonate). The intermediary is reacted (i.e., subjected to thermolysis) under suitable conditions in the presence of a suitable catalyst (e.g., a zeolite) to obtain a methylene malonate monomer. In an exemplary embodiment, the ther-
(Continued)

molysis reaction includes the addition of the bis(hydroxymethyl) malonate intermediary onto a heated catalyst. The reaction product is collected and purified. The disclosed methods may be performed in a continuous operation. Discrete steps may be performed by using modular units within a plant.

16 Claims, 7 Drawing Sheets

Related U.S. Application Data continuation of application No. 14/636,402, filed on Mar. 3, 2015, now Pat. No. 9,108,914, which is a continuation of application No. PCT/US2014/011068, filed on Jan. 10, 2014.

(60) Provisional application No. 61/751,366, filed on Jan. 11, 2013, provisional application No. 61/896,926, filed on Oct. 29, 2013.

(51) Int. Cl.
| | |
|---|---|
| B01J 29/40 | (2006.01) |
| C07C 67/31 | (2006.01) |
| C07C 67/327 | (2006.01) |
| C07C 67/333 | (2006.01) |
| C07C 67/56 | (2006.01) |
| C07C 69/593 | (2006.01) |
| C09J 4/00 | (2006.01) |
| C09D 4/00 | (2006.01) |
| C08F 222/14 | (2006.01) |

(52) U.S. Cl.
CPC .......... *C07C 67/327* (2013.01); *C07C 67/333* (2013.01); *C07C 67/56* (2013.01); *C07C 69/593* (2013.01); *C09J 4/00* (2013.01); *B01J 2208/00168* (2013.01); *B01J 2208/065* (2013.01); *B01J 2219/0004* (2013.01); *B01J 2219/00033* (2013.01); *B01J 2219/00087* (2013.01); *B01J 2219/00177* (2013.01); *B01J 2219/24* (2013.01); *C08F 222/14* (2013.01); *C09D 4/00* (2013.01)

(58) Field of Classification Search
CPC . B01J 19/245; B01J 29/00; B01J 29/04; B01J 29/06; B01J 29/40; B01J 2208/00–2208/00017; B01J 2208/00106; B01J 2208/00168; B01J 2208/06; B01J 2208/065; B01J 2219/00–2219/00002; B01J 2219/00027; B01J 2219/00033; B01J 2219/0004; B01J 2219/00049; B01J 2219/00051; B01J 2219/00074; B01J 2219/00087; B01J 2219/00177; B01J 2219/24; C07C 67/00; C07C 67/30; C07C 67/31; C07C 67/317; C07C 67/327; C07C 67/333; C07C 67/48; C07C 67/56; C07C 69/00; C07C 69/52; C07C 69/593; C08F 222/00; C08F 222/10; C08F 222/12; C08F 222/14; C09D 4/00; C09J 4/00
See application file for complete search history.

(56) References Cited

U.S. PATENT DOCUMENTS

| | | | |
|---|---|---|---|
| 2,403,791 A | 7/1941 | D'Aiello |
| 2,277,479 A | 3/1942 | D'Aiello |
| 2,313,501 A | 3/1943 | Bryant |
| 2,330,033 A | 9/1943 | D'Alelio |
| 3,042,710 A | 7/1962 | Dickstein et al. |
| 3,203,915 A | 8/1965 | D'Alelio |
| 3,221,745 A | 12/1965 | Coover, Jr. |
| 3,427,250 A | 2/1969 | Haas et al. |
| 3,489,663 A | 1/1970 | Bayer et al. |
| 3,523,097 A | 8/1970 | Coover, Jr. |
| 3,557,185 A | 1/1971 | Ito |
| 3,197,318 A | 7/1971 | Halpern et al. |
| 3,591,676 A | 7/1971 | Hawkins |
| 3,595,869 A | 7/1971 | Shuman |
| 3,677,989 A | 7/1972 | Jenkinson |
| 3,758,550 A | 9/1973 | Eck et al. |
| 3,923,836 A | 12/1975 | Bender et al. |
| 3,936,486 A | 2/1976 | Egger et al. |
| 3,940,362 A | 2/1976 | Overhurlts |
| 3,945,891 A | 3/1976 | Aal et al. |
| 3,966,562 A | 6/1976 | Mukushi et al. |
| 3,975,422 A | 8/1976 | Buck |
| 3,978,422 A | 8/1976 | Rheinfelder |
| 3,995,489 A | 12/1976 | Smith et al. |
| 4,001,345 A | 1/1977 | Gorton et al. |
| 4,004,984 A | 1/1977 | Margen |
| 4,018,656 A | 4/1977 | Rogers et al. |
| 4,035,243 A | 7/1977 | Katz et al. |
| 4,036,985 A | 7/1977 | Amato et al. |
| 4,046,943 A | 9/1977 | Smith et al. |
| 4,049,698 A | 9/1977 | Hawkins et al. |
| 4,056,543 A | 11/1977 | Ponticello |
| 4,079,058 A | 3/1978 | Ackermann et al. |
| 4,080,238 A | 3/1978 | Wolinski et al. |
| 4,083,751 A | 4/1978 | Choi et al. |
| 4,102,809 A | 7/1978 | Smith et al. |
| 4,105,688 A | 8/1978 | Arni et al. |
| 4,140,584 A | 2/1979 | Margen |
| 4,148,693 A | 4/1979 | Williamson |
| 4,154,914 A | 5/1979 | Kuraya |
| 4,160,864 A | 7/1979 | Ponticello et al. |
| 4,176,012 A | 11/1979 | Bryant |
| 4,186,058 A | 1/1980 | Katz et al. |
| 4,186,060 A | 1/1980 | Katz et al. |
| 4,198,334 A | 4/1980 | Rasberger |
| 4,224,112 A | 9/1980 | Childs |
| 4,229,263 A | 10/1980 | Childs |
| 4,236,975 A | 12/1980 | Childs |
| 4,237,297 A | 12/1980 | Rody et al. |
| 4,243,493 A | 1/1981 | Gruber et al. |
| 4,256,908 A | 3/1981 | Nishimura et al. |
| 4,282,067 A | 8/1981 | Katz et al. |
| 4,282,071 A | 8/1981 | Sherrod |
| 4,291,171 A | 9/1981 | Baum et al. |
| 4,313,865 A | 2/1982 | Teramoto et al. |
| 4,319,964 A | 3/1982 | Katz et al. |
| 4,329,479 A | 5/1982 | Yabutani et al. |
| 4,396,039 A | 8/1983 | Klenk et al. |
| 4,399,300 A | 8/1983 | Prange et al. |
| 4,411,740 A | 10/1983 | Flanigam et al. |
| 4,440,601 A | 4/1984 | Katz et al. |
| 4,440,910 A | 4/1984 | O'Connor |
| 4,443,624 A | 4/1984 | Prange et al. |
| 4,444,928 A | 4/1984 | Karrer |
| 4,450,067 A | 5/1984 | Angevine et al. |
| 4,504,658 A | 3/1985 | Narisada et al. |
| 4,510,273 A | 4/1985 | Miura et al. |
| 4,517,105 A | 5/1985 | Laemmle et al. |
| 4,539,423 A | 9/1985 | Itatani et al. |
| 4,556,649 A | 12/1985 | Salzburg et al. |
| 4,560,723 A | 12/1985 | Millet et al. |
| 4,578,503 A | 3/1986 | Ishikawa et al. |
| 4,584,064 A | 4/1986 | Ciais et al. |
| 4,613,658 A | 9/1986 | Mathias et al. |
| 4,698,333 A | 10/1987 | Fauss et al. |
| 4,720,543 A | 1/1988 | McPherson et al. |
| 4,728,701 A | 3/1988 | Jarvis et al. |
| 4,736,056 A | 4/1988 | Smith et al. |
| 4,767,503 A | 8/1988 | Crescentini et al. |
| 4,769,464 A | 9/1988 | Sajtos |
| 4,783,242 A | 11/1988 | Robbins |
| 4,835,153 A | 5/1989 | Kabota et al. |

(56) References Cited

U.S. PATENT DOCUMENTS

| | | |
|---|---|---|
| 4,897,473 A | 1/1990 | Dombek |
| 4,914,226 A | 3/1990 | Di Trapani et al. |
| 4,931,584 A | 6/1990 | Bru-Magniez et al. |
| 4,932,584 A | 6/1990 | Yamazaki et al. |
| 5,021,486 A | 6/1991 | Galbo |
| 5,039,720 A | 8/1991 | Saatweber et al. |
| 5,064,507 A | 11/1991 | O'Donnell et al. |
| 5,142,098 A | 8/1992 | Bru-Magniez et al. |
| 5,162,545 A | 11/1992 | Etzbach et al. |
| 5,210,222 A | 5/1993 | O'Murchu |
| 5,227,027 A | 7/1993 | Topper |
| 5,259,835 A | 11/1993 | Clark et al. |
| 5,284,987 A | 2/1994 | Sikkenga et al. |
| 5,292,937 A | 3/1994 | Manning et al. |
| 5,328,687 A | 4/1994 | Leung et al. |
| 5,312,864 A | 5/1994 | Wenz et al. |
| 5,334,747 A | 8/1994 | Steffen |
| 5,426,203 A | 6/1995 | Sohn et al. |
| 5,446,195 A | 8/1995 | Pacifici |
| 5,514,371 A | 5/1996 | Leung et al. |
| 5,514,372 A | 5/1996 | Leung et al. |
| 5,550,172 A | 8/1996 | Regula et al. |
| 5,565,525 A | 10/1996 | Morimoto et al. |
| 5,567,761 A | 11/1996 | Song |
| 5,575,997 A | 11/1996 | Leung et al. |
| 5,582,834 A | 12/1996 | Leung et al. |
| 5,624,669 A | 4/1997 | Leung et al. |
| 5,693,621 A | 12/1997 | Toepfer et al. |
| 5,817,742 A | 10/1998 | Toepfer et al. |
| 5,817,870 A | 10/1998 | Haas et al. |
| 5,886,219 A | 3/1999 | Steffen |
| 5,902,896 A | 5/1999 | Bauer |
| 5,952,407 A | 9/1999 | Rasoul et al. |
| 6,069,261 A | 5/2000 | Hoffmann et al. |
| 6,106,807 A | 8/2000 | Albayrak et al. |
| 6,143,352 A | 11/2000 | Clark et al. |
| 6,183,593 B1 | 2/2001 | Narang et al. |
| 6,210,474 B1 | 4/2001 | Romano, Jr. et al. |
| 6,211,273 B1 | 4/2001 | Bru-Magniez et al. |
| 6,225,038 B1 | 5/2001 | Smith et al. |
| 6,238,896 B1 | 5/2001 | Ozaki et al. |
| 6,245,933 B1 | 6/2001 | Malofsky et al. |
| 6,284,915 B2 | 9/2001 | Hirase et al. |
| 6,291,703 B1 | 9/2001 | Schaerfl et al. |
| 6,376,019 B1 | 4/2002 | Leung |
| 6,395,737 B1 | 5/2002 | Defossa et al. |
| 6,395,931 B1 | 5/2002 | Carvalho et al. |
| 6,413,415 B1 | 7/2002 | Weiss et al. |
| 6,420,468 B2 | 7/2002 | Bru-Magniez et al. |
| 6,440,461 B1 | 8/2002 | Bru-Magniez et al. |
| 6,512,023 B1 | 1/2003 | Malofsky et al. |
| 6,518,677 B1 | 2/2003 | Capote |
| 6,545,097 B2 | 4/2003 | Pinchuk et al. |
| 6,559,264 B1 | 5/2003 | Konig et al. |
| 6,610,078 B1 | 8/2003 | Bru-Magniez et al. |
| 6,613,934 B1 | 9/2003 | Jegelka et al. |
| 6,673,957 B2 | 1/2004 | Bartek et al. |
| 6,699,928 B2 | 3/2004 | Cobbley et al. |
| 6,716,355 B1 | 4/2004 | Hanemaaijer et al. |
| 6,750,298 B1 | 6/2004 | Bru-Magniez et al. |
| 6,794,365 B2 | 9/2004 | Al-Obeidi et al. |
| 6,841,064 B1 | 1/2005 | Weiss et al. |
| 6,936,140 B2 | 8/2005 | Paxton et al. |
| 7,070,675 B2 | 7/2006 | Schmidt et al. |
| 7,109,369 B2 | 9/2006 | Nose et al. |
| 7,208,621 B2 | 4/2007 | Nose et al. |
| 7,226,957 B1 | 6/2007 | Scranton et al. |
| 7,305,850 B2 | 12/2007 | Tonkovich et al. |
| 7,553,989 B2 | 6/2009 | Sawabe et al. |
| 7,603,889 B2 | 10/2009 | Cypes et al. |
| 7,610,775 B2 | 11/2009 | Tonkovich et al. |
| 7,649,108 B2 | 1/2010 | Schal et al. |
| 7,659,423 B1 | 2/2010 | McArdle |
| 7,663,000 B2 | 2/2010 | Dekkers et al. |
| 7,771,567 B2 | 8/2010 | Rives et al. |
| 7,900,558 B2 | 3/2011 | Yokoi |
| 8,609,885 B2 | 12/2013 | Malofsky et al. |
| 8,884,051 B2 | 11/2014 | Malofsky et al. |
| 9,108,914 B1 | 8/2015 | Malofsky et al. |
| 9,181,365 B2 | 11/2015 | Malofsky et al. |
| 9,217,098 B1 | 12/2015 | Stevenson et al. |
| 9,221,739 B2 | 12/2015 | Malofsky et al. |
| 9,234,107 B2 | 1/2016 | Malofsky et al. |
| 9,334,430 B1 | 5/2016 | Stevenson et al. |
| 9,522,381 B2 * | 12/2016 | Malofsky ............... C07C 67/56 |
| 2001/0005572 A1 | 6/2001 | Lobo et al. |
| 2001/0034300 A1 | 10/2001 | Yurugu et al. |
| 2002/0143128 A1 | 10/2002 | Cabioch et al. |
| 2002/0151629 A1 | 10/2002 | Buffkin et al. |
| 2003/0096069 A1 | 5/2003 | D'Alessio |
| 2003/0199655 A1 | 10/2003 | Yurugi et al. |
| 2004/0076601 A1 | 4/2004 | Bru-Magniez et al. |
| 2004/0082043 A1 | 4/2004 | Yadav et al. |
| 2004/0220060 A1 | 11/2004 | Bartley et al. |
| 2006/0167267 A1 | 7/2006 | Chorghade et al. |
| 2006/0211809 A1 | 9/2006 | Kodemura et al. |
| 2007/0043145 A1 | 2/2007 | Beck et al. |
| 2007/0049655 A1 | 3/2007 | Yoshimune et al. |
| 2007/0092483 A1 | 4/2007 | Pollock |
| 2007/0120630 A1 | 5/2007 | Huang et al. |
| 2008/0131618 A1 | 6/2008 | Nakamura et al. |
| 2008/0160305 A1 | 7/2008 | Warren et al. |
| 2008/0187655 A1 | 8/2008 | Markle et al. |
| 2008/0227919 A9 | 9/2008 | Li et al. |
| 2008/0241485 A1 | 10/2008 | Shimohara et al. |
| 2008/0286333 A1 | 11/2008 | Kangas et al. |
| 2009/0203861 A1 | 8/2009 | Lee et al. |
| 2009/0263604 A1 | 10/2009 | Arai et al. |
| 2010/0016508 A1 | 1/2010 | Sasagawa et al. |
| 2010/0256720 A1 | 10/2010 | Overstreet et al. |
| 2010/0286433 A1 | 11/2010 | Malofsky et al. |
| 2010/0286438 A1 | 11/2010 | Malofsky et al. |
| 2011/0015406 A1 | 1/2011 | Umentani et al. |
| 2011/0024392 A1 | 2/2011 | Sato et al. |
| 2011/0164322 A1 | 7/2011 | Morozumi et al. |
| 2012/0083523 A1 | 4/2012 | Richard et al. |
| 2012/0136130 A1 | 5/2012 | Takashima et al. |
| 2013/0281580 A1 | 10/2013 | Malofsky et al. |
| 2013/0303719 A1 | 11/2013 | Malofsky et al. |
| 2014/0058031 A1 | 2/2014 | Overbeek et al. |
| 2014/0248485 A1 | 9/2014 | Malofsky et al. |
| 2014/0275400 A1 | 9/2014 | Chen et al. |
| 2014/0288230 A1 | 9/2014 | Malofsky et al. |
| 2014/0329980 A1 | 11/2014 | Malofsky et al. |
| 2015/0056879 A1 | 2/2015 | Malofsky et al. |
| 2015/0104660 A1 | 4/2015 | Malofsky et al. |
| 2015/0148480 A1 | 5/2015 | Ellison et al. |
| 2015/0210894 A1 | 7/2015 | Malofsky et al. |
| 2015/0303122 A1 | 10/2015 | Malofsky et al. |
| 2015/0361283 A1 | 12/2015 | Malofsky et al. |

FOREIGN PATENT DOCUMENTS

| | | |
|---|---|---|
| FR | 2788516 A1 | 7/2000 |
| GB | 432628 A | 7/1935 |
| GB | 965676 | 8/1964 |
| GB | 965767 | 8/1964 |
| GB | 975733 | 11/1964 |
| JP | H02281013 | 11/1990 |
| JP | H08231564 | 9/1996 |
| JP | 09258448 A | 10/1997 |
| JP | 2000199936 | 7/2000 |
| JP | 2008/174494 | 1/2007 |
| WO | 1999/046619 | 9/1999 |
| WO | 1999/055394 A1 | 11/1999 |
| WO | 2007/120630 A2 | 10/2007 |
| WO | 2010/129068 A1 | 11/2010 |
| WO | 2011/059104 A1 | 5/2011 |
| WO | 2011/161045 A1 | 12/2011 |
| WO | 2012/054633 A2 | 4/2012 |
| WO | 2012054616 A2 | 4/2012 |
| WO | 2013/059473 | 4/2013 |
| WO | 2013/066629 | 5/2013 |

(56) References Cited

FOREIGN PATENT DOCUMENTS

| | | |
|---|---|---|
| WO | 2013/149165 A1 | 10/2013 |
| WO | 2013/149168 A1 | 10/2013 |
| WO | 2013/149173 A1 | 10/2013 |

OTHER PUBLICATIONS

Final Rejection from the State Intellectual Property Office of the People's Republic of China for Application No. 201480003455.7, dated Jun. 14, 2017.
Name Reaction, "Knoevenagel Condensation" Retrieved at <http://www.name-reaction.com/knoevenagel-condensation> last accessed on Oct. 10, 2017.
Organic Chemistry Portal, "Knoevenagel Condensation, Doebner Modification" Retrieved from <http://www.organic-chemistry.org/namedreactions/knoevenagel-condensation.shtm>, last accessed Oct. 10, 2017.
Sigma-Aldrich, "Knoevenagel Condensation Reaction" Retrieved from < http://www.sigmaaldrich.com/technical-documents/articles/chemistry/knoevenagel-condensation-reaction.html> last accessed Oct. 10, 2017.
M. Matziari et al. Active Methylene Phosphinic Peptides: A new Diversification Approach Organic Letters 2006 vol. 8, No. 11 pp. 2317-2319. May 5, 2006.
Zaragoza Dorwald, Side Reactions in Organic Synthesis, 2005, WILEY-VCH Verlag GmbH & Co., KgaA, Weinheim, Preface. p. IX.
K. Okamura and T. Date, A Facile Conversion of Ethoxydihydropyrans to 4-Cyanoethylisoxazoles, J. Heterocyclic Chem. 33, 383 (1996).
NPL Yamauchi et al. Tetrahedron Asymetry 12, (2001), 3113-3118.
Cristoph Schotes et al. "Cu(I)- and C(II)- Catalyzed Cyclo- and Michael Addition Reactions of Unsaturated [beta]-Ketoesters" The Journal of Organic Chemistry, vol. 76, No. 14 dated Jul. 15, 2011 p. 5862-5866.
Alejandro Bugarin et al. "Efficient direct [alpha]-methylenation of carbonyls mediated by dissopropylammonium trifluoroacetate", Chemical Communications, vol. 46, No. 10 dated Jan. 25, 2010.
H. Hoffman et al. "Preparation and Selected Reaction of tery-Butyl 2-Methylene-3-oxoalkanoates" Chem. Ber., vol. 124 dated Jan. 1, 1991, pp. 2475-2480.
M. Yamauchi et al. "Reactivity of 2-Methylene-1, 3-dicarbonyl Compounds. 1,3-Dipolar Cycloaddition Reaction with Ethyl Diazoacetate", Chem. Pham. Bull., vol. 49, No. 12, dated Jun. 25, 2001, pp. 1638-1639.
Lawrence N J et al. "Reaction of Baylis-Hillman products with Swern and Dess-Martin oxidants", Tetrahedron Letters, Pergamon, GB, vol. 42 No. 23 dated Jun. 4, 2001, pp. 3939-3941.
Juliana Vale et al. "Efficient [alpha]-Methylenation of Carbonyl Compounds in Ionic Liquids at Room Temperature", SYNLETT, vol. 2009, No. 01, Jan. 1, 2009 (Jan. 1, 2009), pp. 75-78, XP055170349, ISSN: 0936-5214, DOI: 10.1055/s-0028-1087389.
P. Breton et al., "New Poly(Methylidudene Malonate 2.1.2) Nanoparticles: Recent Developments", Targeting of Drugs 4, NATO ASI Series, vol. 273, pp. 161-172, 1994.
Limouzin et al., "Anionic Polymerization of n-Butyl Cyanoacrylate in Emulsion and Miniemulsion" Macromolecules, vol. 36, 2003, pp. 667-674.
McCoy, M. "A New Way to Stick" Chemical & Engineering News, vol. 92, Issue 26, Jun. 30, 2014, pp. 17-18, paragraph [2].
Bachman et al., "Diethyl Methylenemalonate" Contirbution from the Research Laboratories of the Eastman Kodak Company, May 17, 1939, pp. 493-501.
"Knoevenagel reaction on a molecular sieve", Li Qifang et al., Chinese Science Bulletin, 1988, vol. 12, pp. 914-917.
"Knoevenagel Condensation Over Acidic Zeolite", Zuo Bojun et al., Chinese Journal of Catalysis, Nov. 2002, vol. 23 (6), pp. 555-558.
"Comparison of the catalytic activity of MOFs and zeolites in Knoevenagel condensation", Maksym Opanasenko, et al., Catalysis Science & Technology, 2013, vol. 3, p. 500-507.

Corey et al. "Total Synthesis of Gibberellic Acid. A Simple Synthesiss of a Key Intermediate", J. Am. Chem. Soc. 1982, 104, 6129-6130.
Krishna et al. "Stereodefined Access to 3-Deoxy Sugars Through a Tandem Baylis-Hillman and Lewis Acid Catalyzed Sequence", European Journal of Organic Chemistry, 2010, 813-817.
Gill, Charansingh, et al. "Knoevenagel condensation in neutral media: A simple and efficient protocol for the synthesis of electrophillic alkenes catalyzed by anhydrous ferric sulphate with remarkable reusability." Bulletin of the Catalysis Society of India 7 (2008): 153-157.
State Intellectual Property Office, P. R. China Office Action for Application No. 201480003455.7 dated Mar. 28, 2016.
Extended European Search Report from the European Patent Office for Application No. EP14737563.8, dated Sep. 8, 2016.
International Search Report and Written Opinion for PCT Application No. PCT/US2014/011068 dated May 12, 2014.
M. Ware et al.: "DBU: An Efficient Catalyst for Knoeveganel Condensation under Solvent-free Condition," Bulletin of the Catalysis Society of India, (2007), vol. 6, pp. 104-106.
V. G. Nenajdenko et al.: "Reaction of 2-Methylene-1 ,3-Dicarbonyl Compounds Containing a CF3-Group with 1 ,3-Dienes," Tetrahedron, (2000), vol. 56, pp. 6549-6556.
J. S. Yadav et al.: "Phosphane-Catalyzed Knoevenagel Condensation: a Facile Synthesis of α-Cyanoacrylates and a-Cyanoacrylonitriles," Eur. J. Orq. Chem. (2004), pp. 546-551.
B. C. Ranu et al.: "Ionic Liquid as Catalyst and Reaction Medium—a Simple, Efficient and Green Procedure for Knoevenagel Condensation of Aliphatic and Aromatic Carbonyl Compounds Using a Task-Specific Basic Ionic Liquid," Euro. J. Org. Chem., (2006), pp. 3767-3770.
H. A. Oskooie et al.: "On Water: an Efficient Knoevenagel Condensation using 12-Tungstophosphoric Acid as a Reusable Green Catalyst," Synthetic Communications, (2006), vol. 36, pp. 2819-2823.
H. Jiang et al.: "Inorganic Zinc Salts Catalyzed Knoevenagel Condensation at Room Temperature without Solvent," Preparative Biochemistry & Biotechnology, (2009), vol. 39, pp. 194-200.
B. M. Reddyet al.: "An Easy-to-use Heterogeneous Promoted Zirconia Catalyst for Knoevenagel Condensation in liquid Phase under Solvent-Free conditions," Journal of Molecular Catalysis A: Chemical, (2006), vol. 258, pp. 302-307.
D. H. Jung et al.: "New and General Methods for the Synthesis of Arylmethylene Bis(3- Hydroxy-2-Cyclohexene-1-0nes) and Xanthenediones by EDDA and In(OTf)3-Catalyzed One-Pot Domino Knoevenagel/Michael or Koevenagel/Michael/Cyclodehydration Reactions," Bull. Korean Chem. Soc. (2009) vol. 30, No. 9, pp. 1989-1995.
P. Klemarczyk: "Adhesion Studies of Mixtures of Ethyl Cyanoacrylate with a Difunctional Cyanoacrylate Monomer and with other Electron-deficient Olefins," J. Adhesion, (1999), vol. 69, pp. 293-306.
P. Klemarwczyk: "A General Synthesis of 1,1 Disubstituted Electron Deficient Olefins and their Polymer Properties," Polymer, (1998), vol. 39, No. 1, pp. 173-181.
C. Gill et al.: "Knoevenagel Condensation in Neutral Media: A simple and efficient protocol for the Synthesis of Electrophillic alkenes Catalyzed by Anhydrous Ferric Sulphate with Remarkable Reusability," Department of Chemistry, Dr. Babasaheb Ambedkar Marathwada University, Auran!=labad 431 004 (MS), India, (n/a), pp. n/a.
P. Ballesteros et al.: "DI-tert-Butyl Methylenemalonate [Propanedioic Acid, Methylene-, bis(1, 1-dimethylethyl)ester]," Organic Syntheses. Coil. (1990), vol. 7, p. 142 ; (1986) vol. 64, p. 63.
A. M. Vetrova et al.: "Improvement of the Thermal Stability of Cyanoacrylate Adhesives,"Polymer Science, Series D, (2009), vol. 2, No. 1, pp. 27-30.
A. C. Cope: "Condensation Reactions. I. The Condensation of Ketones with Cyanoacetic Esters and the Mechanism of the Knoevenagel Reaction," Condensation of Ketones with Cyanoacetic Esters, (1937), vol. 59, pp. 2327-2330.
G. Lai et al.: "Ionic Liquid Functionalized Silica Gel: Novel Catalyst and Fixed Solvent,"Tetrahedron Letters (2006), vol. 47, pp. 6951-6953.

(56) References Cited

OTHER PUBLICATIONS

J. R. Harjani et al.: "Lewis Acidic Ionic Liquids for the Synthesis of Electrophilic Alkenes via the Knoevenagel Condensation," Tetrahedron Letters, (2002), vol. 43, pp. 1127-1130.
P. Ballesteros et al.: "Synthesis of DI-tert-Butyl Methylenemalonate, a Sterically Hindered 1,1-Dicarbonyl Alkene," J. Org. Chem, (1983), vol. 48, pp. 3603-3605.
T. Doi et al.: "Synthesis of Dimethyl gloiosiphne A by Way of Palladium-Catalyzed Domino Cyclization," J. Org. Chem., (2007), vol. 72, pp. 3667-3671.
Takagi et al.: Kogyo Kagaku Zasshi, Reaction of Active Methylene Radicals with Formaldehyde. L. Synthesis of Diethyl Methylenemalonate, 1953, 56, pp. 901-903, English abstract.
McNab, Kirk-Othmer Encyclopedia of chemical Technology, Pyrolysis, Flash Vacuum, 2009, John Wiley & Sons, Inc., pp. 1-26.
Block, "Diethyl bis (hydroxymethyl) malonate "Organic Syntheses, 1973, Coll. vol. 5, p. 381 [vol. 40, p. 27 (1960); Retrieved on Apr. 4, 2014 from internet: http://www.Orgsyn.org/content/pdfs/procedures/cv5p0381.pdf] p. 381, para 1.
Co-Pending U.S. Appl. No. 14/536,753, filed Nov. 10, 2014.
Ballesteros et al, Organic Syntheses, Di-tert-Butyl Methylene Malonate [Propanedioic acid, methylene-,bis(1, 1-dimethylethyl ester], 1990, Coll. vol. 7, p. 142.
White et al, Baisc Energy Sciences Advisory Committee Subpanel Workshop Report, Opportunities for Catalysis in the $21^{st}$ Century, 2002, pp. 1-47.

\* cited by examiner

METHOD TO OBTAIN METHYLENE MALONATE VIA BIS(HYDROXYMETHYL) MALONATE PATHWAY

CROSS-REFERENCE TO RELATED APPLICATIONS

This application is a continuation of U.S. patent application Ser. No. 14/823,581, now U.S. Pat. No. 9,522,381, filed Aug. 11, 2015, which is a continuation of U.S. patent application Ser. No. 14/636,402 now U.S. Pat. No. 9,108,914, filed Mar. 3, 2015, which is a continuation of International Patent Application PCT/US2014/011068, now WO/2014/110388, filed on Jan. 10, 2014 and claims priority to U.S. Provisional Patent Application 61/751,366 filed Jan. 11, 2013, entitled Method to Obtain Methylene Malonate via Bis(hydroxymethyl) malonate Pathway, and to U.S. Provisional Patent Application 61/896,926, filed Oct. 29, 2013, entitled Method and Apparatus to Produce Methylene Malonates and Related Matetials, the contents of each of which are hereby incorporated herein by reference in their entirety.

INCORPORATION BY REFERENCE

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

BACKGROUND OF THE INVENTION

1. Field of the Invention

The invention relates to the production of methylene malonate species using a bis(hydroxymethyl) malonate intermediary. The intermediary is subsequently cracked to yield a monomer species.

2. Background

A class of polymerizable compositions of interest includes methylene malonates. Methylene malonates are compounds having the general formula (I):

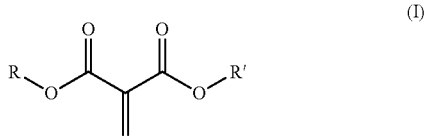

(I)

wherein R and R' may be the same or different and may represent nearly any substituent or side-chain. Such compounds have been known since 1886 where the formation of diethyl methylene malonate was first demonstrated by W. H. Perkin, Jr. (Perkin, Ber. 19, 1053 (1886)).

Methylene malonate monomers and their associated monomeric and polymeric-based products would be useful in both industrial (including household) and medical applications.

However, while earlier methods for producing methylene malonates have been known for many years, these prior methods suffer significant deficiencies that preclude their use in obtaining commercially viable monomers. Such deficiencies include unwanted polymerization of the monomers during synthesis (e.g., formation of polymers or oligomers or alternative complexes), formation of undesirable side products (e.g., ketals or other latent acid-forming species which impede rapid polymerization), degradation of the product, insufficient and/or low yields, and ineffective and/or poorly functioning monomer product (e.g., poor adhesive characteristics, stability, or other functional characteristics), among other problems. The overall poorer yield, quality, and chemical performance of the monomer products formed by prior methods have impinged on their practical use in the production of the above commercial and industrial products.

Certain co-inventors of the instant application have filed patent applications on improved methods of synthesis of methylene malonates, namely, WO 2012/054616 Synthesis of Methylene Malonates Substantially Free of Impurities, and WO 2012/054633 Synthesis of Methylene Malonates Using Rapid Recovery in the Presence of a Heat Transfer Agent. The synthesis procedures provided therein result in improved yields of heretofore-elusive high quality methylene malonates and other polymerizable compositions.

While the improved methods disclosed in the above-identified patent applications are able to provide the desired methylene malonate monomers, continuous improvements are sought, particularly in the development of methods to provide materials on a commercial scale. Thus, a need exists for improved and/or simplified processes for obtaining methylene malonate and related monomers.

SUMMARY OF THE INVENTION

The purpose and advantages of the present invention will be set forth in and apparent from the description that follows. Additional advantages of the invention will be realized and attained by the methods and systems particularly pointed out m the written description and claims hereof, as well as from the appended drawings.

The present invention provides novel methods for the preparation of methylene malonate monomers from a bis (hydroxymethyl) malonate reagent in the presence of a catalyst; polymers thereof, and products using said monomers and polymers.

In one aspect, the invention provides a method of making a methylene malonate monomer comprising:

(a) reacting a dialkyl bis(hydroxymethyl) malonate composition in the presence of a suitable catalyst to form a methylene malonate monomer; and (b) isolating the methylene malonate monomer.

In certain embodiments, the reacting step (a) is accomplished in a continuous process.

In certain embodiments, the reacting step (a) is accomplished without the addition of a solvent.

In certain embodiments, the reacting step (a) is accomplished under atmospheric pressure.

In certain embodiments, each alkyl of the dialkyl bis (hydroxymethyl) malonate may be the same or different and is a straight or branched hydrocarbon group having between 1 and 16 carbon atoms.

In one embodiment of the method of the invention, the dialkyl bis(hydroxymethyl) malonate composition is prepared by a method comprising:

(i) reacting a source of formaldehyde with a dialkyl malonate ester in the presence of a reaction catalyst to form a diol reaction product comprising the dialkyl bis(hydroxymethyl) malonate composition.

In certain embodiments, the reacting step (i) is accomplished in a continuous process.

In certain embodiments, the reacting step (i) is accomplished without the addition of a solvent.

In certain embodiments, the reacting step (i) is accomplished at atmospheric pressure.

In certain embodiments of step (i), the source of formaldehyde is formaldehyde, trioxane, formalin, or paraformaldehyde. In particular embodiments, of step (i), the source of formaldehyde is formalin. In still other embodiments of step (i), the source of formaldehyde is substantially free of methanol, water, or both. In certain other embodiments of step (i), the reaction catalyst is a basic catalyst. In particular embodiments of step (i), the reaction catalyst is calcium hydroxide.

In another embodiment of the method of the invention, the diol reaction product of step (i) is subjected to a diol purification step (ii) prior to the reaction step (a).

In certain embodiments, the diol purification step (ii) comprises cationically exchanging the diol reaction product of step (i) to produce dialkyl bis(hydroxymethyl) malonate, subjecting the dialkyl bis(hydroxymethyl) malonate to an evaporation step to remove volatile impurities, or a combination thereof. In particular embodiments, the diol purification step (ii) comprises cationically exchanging the diol reaction product of step (i) to produce dialkyl bis(hydroxymethyl) malonate, and subjecting the dialkyl bis(hydroxymethyl) malonate to an evaporation step to remove volatile impurities.

In still another embodiment of the method of the invention, the method further comprises the step of:

c) purifying a thermolysis product obtained in step (a) to obtain the isolated methylene malonate monomer.

In certain embodiments of step (c), the thermolysis product is purified by partial condensation, full condensation, fractional distillation, or any combination thereof.

In some embodiments of the method of the invention, the suitable catalyst is an acidic or basic catalyst. In other embodiments of the method of the invention, the suitable catalyst is a zeolite. In particular embodiments of the method of the invention, the suitable catalyst is an aluminosilicate zeolite. In other exemplary embodiments, the suitable catalyst is a metal zeolite.

In another embodiment of the method of the invention, the suitable catalyst is in the form of a column through which the dialkyl bis(hydroxymethyl) malonate composition is passed. In certain embodiments, the dialkyl bis(hydroxymethyl) malonate composition is passed into the column as a liquid. In other embodiments, the dialkyl bis(hydroxymethyl) malonate composition is passed into the column as a gas.

In some embodiments, the catalyst column is heated to a wall temperature between about 180° C. and about 250° C.; between about 200° C. and about 230° C.; or to about 210° C. In particular embodiments, the temperature of the suitable catalyst is maintained throughout the reaction step.

In some other embodiments, the catalyst column has a diameter of about 0.5 to about 4.0 inches; of about 1.0 to about 3.5 inches; or of about 1.5 to about 3.0 inches. In still other embodiments, the catalyst column has a length of about 3 inches to about 200 inches; of about 12 inches to about 72 inches; or of about 18 inches to about 60 inches.

In still other embodiments, the dialkyl bis(hydroxymethyl) malonate composition is passed into the catalyst column at a rate of about 0.01 to 65 kg/hr; of about 0.5 to 25 kg/hr; or about of 1.5 to 10 kg/hr.

In particular embodiments,
the catalyst column has a diameter 0.5 to about 4.0 inches;
the catalyst column has a length of about 3 inches to about 200 inches; and
the dialkyl bis(hydroxymethyl) malonate composition is passed into the catalyst column at a rate of 0.1 to 65 kg/hr.

In other particular embodiments,
the catalyst column has a diameter of about 1.0 to about 3.5 inches;
the catalyst column has a length of about 12 inches to about 72 inches; and
the dialkyl bis(hydroxymethyl) malonate is passed into the catalyst column at a rate of 0.05 to 25 kg/hr.

In still other particular embodiments,
the catalyst column has a diameter of about 1.5 to about 3.0 inches
the catalyst column has a length of about 18 inches to about 60 inches; and
the dialkyl bis(hydroxymethyl) malonate is passed into the catalyst column at a rate of 1.5 to 15 kg/hr.

In certain embodiments of the method in which a diol purification step is used, the diol reaction product of step (i) is cationically exchanged using an ion-exchange column. In some embodiments, the ion-exchange column is packed with an ion-exchange resin. In still other embodiments, the ion exchange column is a pressurized ion-exchange column. In particular embodiments, the pressurized ion-exchange column is pressurized up to 1000 psi.

In other embodiments of the method in which a diol purification step is used, the evaporation step is performed by a short heat residence time apparatus. In certain embodiments, the evaporation step is performed by wiped-film evaporation, rotary evaporation or horizontal or vertical thin-film evaporation. In particular embodiments, the evaporation step is performed by wiped-film evaporation.

In certain embodiments, the method of the invention is performed as a batch process.

In certain other embodiments, the method of the invention is performed as a continuous process.

In certain embodiments, the dialkyl bis(hydroxymethyl) malonate composition has less than 500 ppm cations, less then 50 ppm cations, or less than 5 ppm cations.

In an exemplary embodiment, the suitable catalyst has a life between generation cycles of greater than 12 hours, greater than 200 hours, or greater than 2000 hours.

In an exemplary embodiment, the suitable catalyst may be regenerated by use of an acid.

In on exemplary embodiment, the dialkyl bis(hydroxymethyl) malonate composition includes between 0 and 30% water, between 0 and 20% water, between 0 and 10% water, between 0 and 5% water, between 0 and 1% water, or between 0 and 0.5% water.

In an exemplary embodiment, the dialkyl bis(hydroxymethyl) malonate composition has between 0 and 0.30% water.

In an exemplary embodiment, the dialkyl bis(hydroxymethyl) malonate composition in a vapor state and includes water as a carrier gas.

In another aspect, the invention provides a methylene malonate monomer prepared according to the method of the invention.

In still another aspect, the invention provides a composition comprising a methylene malonate monomer prepared according to the method of the invention.

In yet another aspect, the invention provides a product comprising a methylene malonate monomer prepared according to the method of the invention, wherein the product is an adhesive composition, a coating composition, a sealant, a composite, or a surfactant.

In certain embodiments, the product of the invention further comprises an acidic stabilizer, a free radical stabilizer, a sequestering agent, a cure accelerator, a rheology modifier, a plasticizing agent, a thixotropic agent, a natural rubber, a synthetic rubber, a filler agent, a reinforcing agent or a combination thereof.

In some embodiments, in which the product comprises an acidic stabilizer, the acid stabilizer has a pKa in the range of −15 to 5. In certain embodiments, the acid stabilizer is present in a concentration of 0.1 ppm to 100 ppm.

In other embodiments, the product comprises a free radical stabilizer. In certain embodiments, the free radical stabilizer is a phenolic free radical stabilizer. In other embodiments, the free radical stabilizer is present in a concentration of 0.1 ppm to 10000 ppm.

In still other embodiments, in which the product comprises a sequestering agent the sequestering agent is a crown ether, a silyl crown, a calixarene, u polyethylene glycol, or a combination thereof.

In yet other embodiments, in which the product comprises a cure accelerator, the cure accelerator is sodium acetate, potassium acetate, tetrabutyl ammonium fluoride, tetrabutyl ammonium chloride, tetrabutyl ammonium hydroxide, a benzoate salt, a 2,4-pentanedionate salt, a sorbate salt, a propionate salt or combinations thereof.

In other embodiments, in which the product comprises a rheology modifier, the rheology modifier is hydroxyethylcellulose, ethyl hydroxyethylcellulose methylcellulose, a polymeric thickener, pyrogenic silica or a combination thereof.

In another aspect the invention provides an adhesive product comprising a methylene malonate monomer prepared according to the methods of the invention.

In still another aspect, the invention provides a polymer comprising one or more units of a methylene malonate monomer prepared according to the methods of the invention.

In yet another aspect, the invention provides a polymer product comprising a polymer comprising one or more units of a methylene malonate monomer prepared according to the methods of the invention. In some embodiments, the polymer product is a sealant, a thermal barrier coating, a textile fiber, a water-treatment polymer, an ink carrier, a paint carrier, a packaging film, a molding, a medical polymer, a polymer film, a polymer fiber or a polymer sheet.

In still another aspect the invention provides a plant for producing a methylene malonate monomer wherein the plant comprises one or more modular units wherein the one or more modular units are diol production units, diol purification units, monomer production units, monomer purification units, or a combinations thereof.

In some embodiments, the plant for producing a methylene malonate monomer according to the invention comprises:
  at least one diol production unit,
  at least one diol purification unit,
  and at least one monomer production unit.

In some embodiments, the plant for producing a methylene malonate monomer according to the invention comprises:
  at least one diol production unit,
  at least one diol purification unit,
  at least one monomer production unit, and
  at least one monomer purification unit.

In some embodiments, the plant for producing a methylene malonate monomer according to the invention comprises:
  at least one monomer production unit, and
  at least one monomer purification unit.

In some embodiments, the plant for producing a methylene malonate monomer according to the invention comprises:
  at least one diol production unit,
  optionally, at least one diol purification unit,
  at least one monomer production unit, and
  optionally, at least one monomer purification unit.

In certain embodiments of the plant of the invention, the diol production unit comprises a diol reactor apparatus capable of reacting a dialkyl malonate ester and a source of formaldehyde in the presence of a reaction catalyst.

In certain other embodiments of the plant of the invention, the diol purification unit comprises an ion-exchange column and a wiped-film evaporation apparatus.

In still other embodiments of the plant of the invention, the monomer production unit comprises at least one catalyst column and a heating apparatus for maintaining the temperature of the at least one catalyst column.

In still other embodiments of the plant of the invention, the monomer production unit comprises a plurality of catalyst columns and at least one heating apparatus for maintaining the temperature of the plurality of catalyst columns.

In still another embodiment of the plant of the invention, the monomer production unit comprises at least a single reactant feed line to feed a plurality of catalyst columns.

In yet other embodiments of the plant of the invention, the monomer purification unit comprises a condensation apparatus, a fractional distillation apparatus, or both.

In certain embodiments of the plant of the invention, the plant having two or more modular units, the modular units are in communication with each other such that the product output of a first unit is input into another unit for reaction; such that
  a first diol production unit is in communication with either a diol purification unit or a monomer production unit,
  a first diol purification unit is in communication with a monomer production unit, or
  a first monomer production unit is in communication with a monomer purification unit.

BRIEF DESCRIPTION OF THE DRAWINGS

So that those having ordinary skill in the art to which the subject invention pertains will more readily understand how to make use the invention as described herein, preferred embodiments thereof will be described in detail below, with reference to the drawings, wherein.

DESCRIPTION OF THE INVENTION

Definitions

Figure 1:
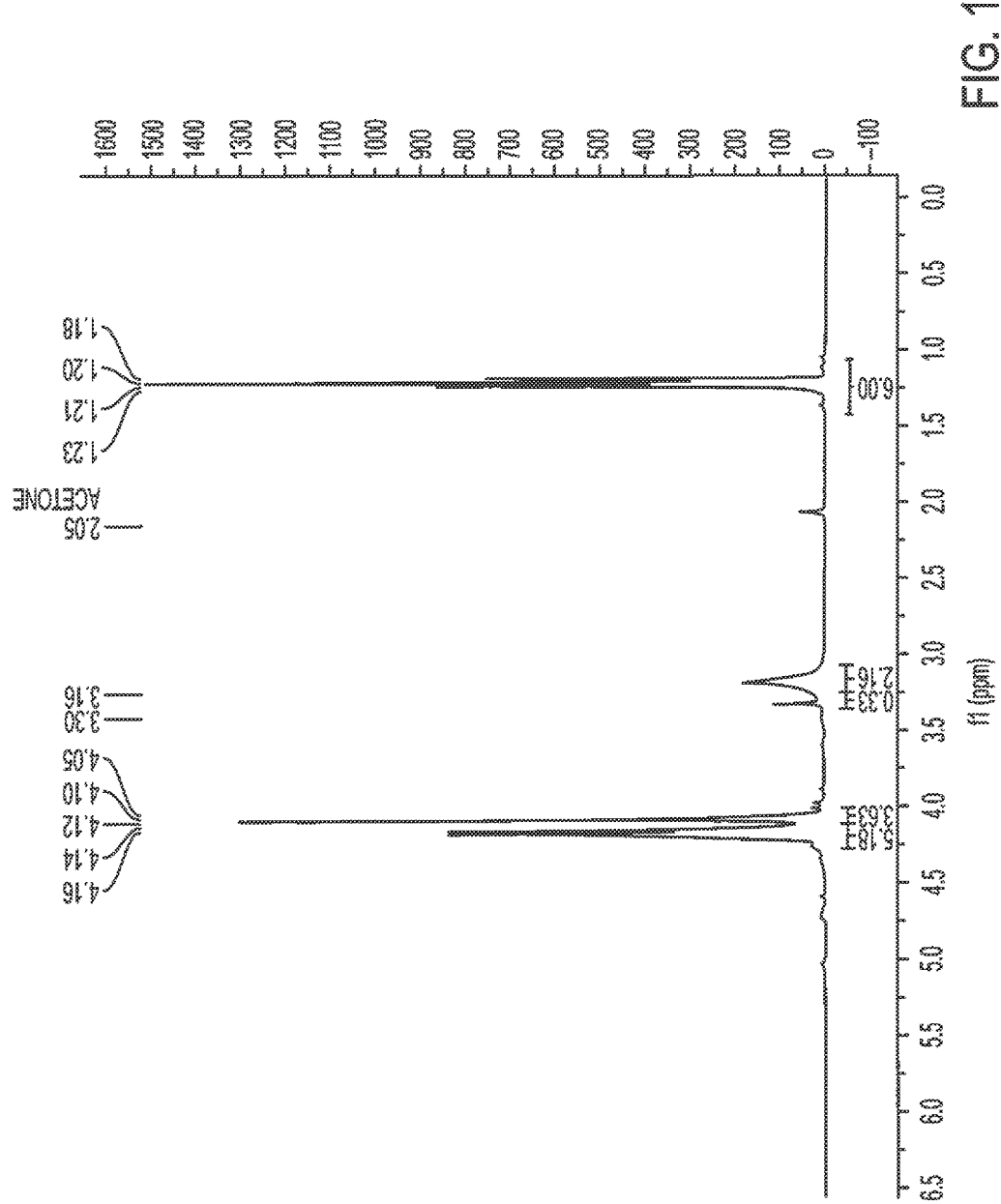
FIG. 1 depicts HNMR showing production of diethyl bis(hydroxymethyl) malonate intermediary.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper (Collins Dictionary of Biology (1991). As used herein, the following terms have the meanings ascribed to them below, unless specified otherwise.

As used herein, the term "methylene malonate" refers to a compound having the core formula

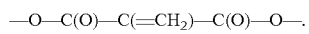

As used herein, the term "bis(hydroxymethyl) malonate" refers to a compound having the core formula

The term "alkyl" includes saturated aliphatic groups, including straight-chain alkyl groups, branched-chain alkyl groups, cycloalkyl (alicyclic) groups, alkyl substituted cycloalkyl groups and cycloalkyl substituted alkyl groups. In certain embodiments, a straight chain or branched chain alkyl has 30 or fewer carbon atoms in its backbone, e.g., C1-C30 for straight chain or C3-C30 for branched chain. In certain embodiments, a straight chain or branched chain alkyl has 20 or fewer carbon atoms in its backbone, e.g., C1-C20 for straight chain or C3-C20 for branched chain, and more preferably 18 or fewer. Likewise, preferred cycloalkyls have from 3-10 carbon atoms in their ring structure and more preferably have 4-7 carbon atoms in the ring structure. The term "lower alkyl" refers to alkyl groups having from 1 to 6 carbons in the chain and to cycloalkyls having from 3 to 6 carbons in the ring structure.

Moreover, the term "alkyl" (including "lower alkyl") as used throughout the specification and claims includes both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phiosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, amino, sulfhydryl, alkylthio, arylthio, thiocarboxylate, sulfate, sulfonate, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl (benzyl). As used herein, the term "monofunctional" refers to a malonic acid ester or a methylene malonate having only one core formula.

As used herein, the term "zeolite" refers to a molecular sieve containing an alumino silicate lattice, usually in association with some aluminum, boron, gallium, iron, and or thallium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

As used herein, the term "reaction product" refers to the materials which result after reacting the reagents of one step of the method of the invention.

As used herein, the term "reaction vessel" refers to any container in which the reactants, solvents, catalysts or other materials may be combined for reaction. Such reaction vessels can be made of any material known to one of skill in the art such as metal, ceramic or glass.

As used herein, the term "recovering" or "obtaining" or "isolating" as in "isolating the methylene malonate monomer," refers to the removal of the monomer from the reaction mixture, vapor phase, or condensed vapor phase by one of the methods described herein so it is in a substantially pure form.

As used herein, the term "short heat residence time apparatus," refers to an apparatus capable of introducing heat to a material sufficient to evaporate volatile materials without subjecting the material to long residence time at the elevated temperature. Exemplary low heat residence apparatuses include wiped-film evaporators, rotary evaporators, horizontal or vertical thin-film evaporators, and the like.

As used herein, the terms "volatile" and "non-volatile" refers to a compound which is capable of evaporating readily at normal temperatures and pressures, in the case of volatile; or which is not capable of evaporating readily at normal temperatures and pressures, in the case of non-volatile. The terms "volatile" and "non-volatile" may also reference relative volatility between materials, as in a first material may be more volatile (i.e., evaporate more readily) than a second material at a given temperature and pressure.

As used herein, the term "maintained," as in "the temperature of the catalyst is maintained" refers to a condition which is substantially the same during the entirety of the reaction process. One of skill in the art will understand that any number of means may be used to maintain a particular condition, for example, heating or cooling for temperature. In general, a property is considered maintained if it remains within 10%, above or below, of the particular condition.

As used herein the term "batch process," refers to a process in which reactant(s) are added to a reaction vessel and one or more of the reactant or product accumulates therein.

As used herein, the term "continuous process," refers to a process in which the reactant(s) are fed to the reaction vessel in a continuous manner without accumulation of reactant(s) or products formed in the reaction. In certain continuous processes, there is a constant feed in as well as a constant feed out. The product may be collected in a product collection vessel or apparatus.

As used herein the term "substantially free" as in "substantially free of methanol or water" refers to a reagent or reaction mixture which comprises less than 1% by weight of the particular component as compared to the total reaction mixture. In certain embodiments, "substantially free" refers to less than 0.7%, less than 0.5%, less than 0.4% less than 0.3%, less than 0.2% or less than 0.1% by weight of the particular component as compared to the total reaction mixture. In certain other embodiments, "substantially free" refers to less than 1.0%, less than 0.7%, less than 0.5%, less than 0.4% m less than 0.3%, less than 0.2% or less than 0.1% by volume of the particular component as compared to the total reaction mixture.

As used herein, the term "stabilized," e.g., in the context of "stabilized" methylene malonates or compositions comprising same, refers to the tendency of the methylene malonates (or their compositions) of the invention to substantially not polymerize with time, to substantially not harden, form a gel, thicken, or otherwise increase in viscosity with time, and/or to substantially show minimal loss in cure speed (i.e., cure speed is maintained) with time.

As used herein, the term "thermolysis" refers to the dissociation of a chemical compound by heat. As used herein, the term "crack," or "cracking" refers to a themolysis process. In certain exemplary embodiments, the term "cracking reaction" refers to the thermolysis of a diakyl bis(hydroxymethyl) malonate to a monomer species with the release of formaldehyde and water.

As used herein, the term "plant" refers to a series of apparatus which are used to perform the methods of the invention. A "plant" can refer to any size of apparatus, including small-scale benchtop apparatus and large-scale commercial apparatus. As used herein, a "plant" may include apparatus housed in multiple locations or the same location.

As used herein, the term "modular unit" refers to a series of apparatus which are used to perform a particular step of the methods of the invention. In certain embodiments, but without being limited thereto, the "modular unit" may be housed in a cabinet, trailer, or other container which may be transported within a particular plant. In other embodiments, the "modular unit" may be fixed within a plant.

As used herein, all percentages (%) refer to weight percent (wt. %) unless otherwise noted.

Any numerical ranges include range endpoints and any sub-ranges contained within the given range.

Exemplary Embodiments

I. Intermediate Production: dialkyl bis(hydroxymethyl) malonate ("Diol")

A robust scalable process giving consistent repeatable well-performing product quality is desired. It has been discovered that limiting and/or identifying impurities added and formed during diol manufacture reduces side reactions in the diol conversion to the desired monomer species. Exemplary embodiments of monomer production are provided. In addition, certain enhancements to the processes are discussed as well. The enhancements may provide improvements in operability, control, yield, rate, robustness, costs, wastes, quality, and ease of scale-up.

In an exemplary embodiment, diol is produced by reacting dialkyl malonate ester and a source of formaldehyde in the presence of a reaction catalyst under suitable reaction conditions. The diol is thereafter collected and treated to prepare for thermolysis for conversion to the desired monomer species. The dialkyl malonate ester may comprise similar or dissimilar alkyl groups. The reactants are provided in about a 2:1 molar ratio of formaldehyde to dialkyl malonate ester. During the reaction two (—$CH_2$—OH) groups are added at the active carbon to produce dialkyl bis(hydroxymethyl) malonate (i.e. "diol").

Suitable reaction catalysts include bases such as calcium hydroxide, calcium carbonate, sodium hydroxide, sodium bicarbonate, amines and polymer supported versions thereof, trialkyl amines, trimethyl amines, triethyl amines, supported bases such as ion exchange resins.

EXAMPLE 1

Diol Production in Continuous Reactor

Diol is produced in a continuous flow reactor. The reactants include a source of formaldehyde, in this instance, a commercially available formalin (37 wt %, stabilized with 7 wt % methanol) and diethyl malonate (DEM). The reaction catalyst is calcium hydroxide. The reaction catalyst (0.17 mol % based on the amount of DEM to be reacted) is dissolved into the formalin (target is 2 moles formaldehyde per mole of DEM) and mixed for approximately 1 hour, or a sufficient time for desired result. The formalin/catalyst mixture was fed into a long static mixer tube. The DEM was injected into a plurality of locations in the static mixer tube. It has been discovered that improved conversion to diol is possible through staged addition of the DEM, in part because the temperature rise due to the exothermic reaction may be more readily controlled. Additionally, the static mixer tube may be maintained in a water bath or other medium to control reaction temperature, as those having skill in the art will readily ascertain. In an exemplary embodiment, the diol production reaction temperature is maintained at about 30 C-40 C. After sufficient reaction time, the reaction may be quenched to prevent or minimize formation of undesired side products. In an exemplary embodiment, because the diol production reaction is catalyzed by a base, a pH lowering agent may optionally be introduced to quench the reaction. In other exemplary embodiments, the reaction kinetics are such that a quenching agent may not be required. In certain exemplary embodiments, the reaction product may include 60-65 wt % diol and about 27 wt % water. Improved diol yields are anticipated through engineering the reaction vessel, close control of reaction temperature, reducing or eliminating the amount of water and/or methanol in the formalin, optimizing catalyst loading, and other reaction optimization methods known to those having skill in the art. During the formation of the diol, it is desired to minimize the formation of unwanted species as they may have adverse effects on diol conversion to monomer.

Figure 7:
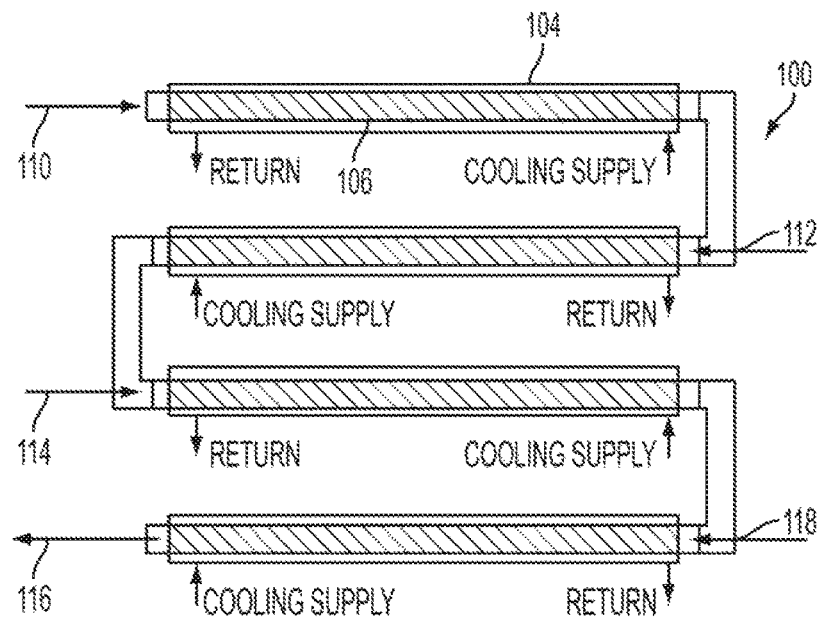
FIG. 7 provides a schematic of a continuous diol production reactor 100.

FIG. 7 provides a schematic of a continuous diol production reactor 100. The reactor 100 includes a shell 104 having a plurality of static mixers 106 distributed along its length. In an exemplary embodiment, the shell 104 may be adapted for cooling to control heat generated by the exothermic reaction. The formalin/catalyst stream 110 is introduced to the reactor 100. The dialkyl malonate ester may be introduced) at a plurality of inlets 112, 114. In the continuous reactor, the desired reaction product, dialkyl bis(hydroxymethyl) malonate, is removed at outlet 116. In an exemplary embodiment, a pH lowering agent, is optionally introduced at inlet 118 to quench the reaction. Those having skill in the art will appreciate that the reactor 100 illustrated here merely illustrates one design and variations or other designs may be successfully utilized to accomplish the purposes of the invention.

EXAMPLE 2

Dial Production in Batch Reactor

The diol production reaction may be conducted in a batch reactor. In an exemplary embodiment, the reaction catalyst (e.g., calcium hydroxide) was added to a premixed solution of formalin and DEM at 22 C. In another exemplary embodiment, the initial reaction temperature was about 10 C. The reaction progresses rapidly and accompanied by a spike in temperature, to about 60-85 C. The reaction product mixture may be allowed to cool naturally, or may be aided through ice baths, cooling coils, etc. After cooling to around 30 C, a pH lowering agent (e.g., HCl, $H_3PO_4$, $H_2SO_4$) was added to the reaction mixture to quench the reaction. The pH was lowered to about 4.5. The reaction product mixture was filtered to remove solids and dried in preparation for thermolysis.

EXAMPLE 3

Metered Reaction

DEM was metered into a premixed solution of formalin and calcium hydroxide. DEM was added and the temperature and pH of the reaction mixture was monitored. When the reaction pH dropped to about 6.5, additional catalyst was added. Using this exemplary procedure, the max maximum reaction temperature ranged from about 35 C to about 44 C. The reaction product mixture was filtered in preparation for thermolysis.

EXAMPLE 4

Heterogeneous Catalyst Reactor

SIR-300 ion-exchange resin in the Na+ form was used in a section of a continuous reactor to produce diol from formalin and DEM. The reactor section included one formalin inlet and one DEM inlet. The formalin and DEM were passed through the weak base resin bed. The material collected at The outlet was passed through the catalyst bed for a total of three passes. The final reaction product comprised from about 23 wt % to about 36 wt % diol.

EXAMPLE 5

Batch Process; Slow Addition of DEM

A 5 L round bottom flask was charged with 37% aqueous formaldehyde (1620 g, 20 mol) and sodium carbonate (45 g, 0.42 mol). With ice water cooling diethyl malonate (1600 g, 10 mol) was slowly added, maintaining temperature between 15-20° C. Following the reaction, the pH of the reaction product mixture was adjusted to between 6 and 7 with 10% HCl. Thereafter, vacuum (100 mm Hg) was applied and the reaction product mixture was warmed to about 45-50° C. to drive off methanol. The reaction product mixture was then cooled to between 20-25° C. NaCl (250 g) was added to the reaction product mixture and stirred for 30 min. The reaction product mixture was then allowed to settle for approximately 1 hour to permit phase separation. The lower aqueous layer was then removed. The organic layer, including the reaction product was dried with anhydrous $Na_2SO_4$ (100 g). The product was filtered and then analyzed by NMR and GCMS. The desired reaction product is diethyl bis(hydroxymethyl) malonate. In an exemplary embodiment yield is 1960 g (89-90%). Purity is 99%. See FIG. 1.

II. Diol Preparation for Thermolysis

In certain exemplary embodiments, following the diol production reaction, the reaction product, comprising the desired diethyl bis(hydroxymethyl) malonate, is subjected to further process steps in preparation for thermolysis. As discussed in certain of the examples provided above, the diol produced by certain routes may benefit from a filtration step. Certain exemplary routes to produce diol may benefit from aqueous wash ups and subsequent drying.

In other exemplary embodiments, the crude diol product is optionally subjected to a cation-exchange process. Excess water (and methanol from commercial formalin) is that optionally removed in a subsequent polishing (drying) step.

EXAMPLE 6

Cation Exchange

In an exemplary embodiment, the reaction product, comprising the diethyl bis(hydroxymethyl) malonate is subjected to an ion-exchange process to exchange cations carried in the reaction product from the reaction catalyst for another cation, particularly H+. Currently, the diol reaction product is fed, as is, from the diol reactor. The ion-exchange column is charged with Resin Tech SIR-300 resin, a macroporous weak acid cation exchange resin based on the iminodiacetate acid functional group, with sodium as the default ion form. Prior to use with the reaction product diol, the resin is acid washed (using 2N HCl) to exchange (Na+) on the resin with ($H^+$). The diol reaction product is then fed through the ion-exchange column to exchange ($Ca^{+2}$) present in the reaction product from the reaction catalyst. The level of decalcification may be monitored by measuring the pH and the conductivity of the efficient from the column. In an exemplary embodiment, a successful ion-exchange results in a pH of about 2.5 to 3 and a conductivity of about 10-15 µS.

Those having skill in the art will appreciate that input flow rates, pressures, column height, exchange resins and the like may be modified in order to achieve a desired polished product, provided at acceptable flow rates for scaled activity.

EXAMPLE 7

Diol Drying (Water Evaporation)

In an exemplary embodiment, diol produced through certain of the examples discussed above may include excess water and residual methanol (present from the commercially stabilized formalin). In exemplary embodiments, a certain water level is desirable as it improves diol handling by preventing the diol from freezing (solidifying) in subsequent reaction steps. However, excess water may cause detrimental side reactions in subsequent processes and will also require removal downstream. Thus, those having skill in the art will appreciate that acceptable water levels in the diol product will balance ease of handling with the difficulty of removal and any deleterious effects it may cause. In an exemplary embodiment, the "dried" diol may comprise up to about 25 wt %, between 1-10 wt %, or between 4 wt %-7 wt % water as compared to the initial feed water level of about 27 wt % and methanol level of about 1.3 wt % ("wet" diol). In other exemplary embodiments the dry diol may include a lower water lever (e.g., about 3.0 wt %, about 2.5 wt %, about 1 wt %).

In an exemplary embodiment, the "wet" diol is introduced into a wiped-film evaporator (WFE) at a predetermined feed rate (e.g., 3 kg/hr). In an exemplary embodiment the WFE is jacketed with a hot oil bath maintained at about 150 C, under about 5 mm Hg vacuum. In an exemplary embodiment, the "dried" diol exiting the WFE contains about 3-5 wt % water, and is substantially free of methanol, as defined herein, or contains very little methanol (less than about 1.3 wt %). If desired, lower water levels are attainable.

In an exemplary embodiment, the WFE is utilized to evaporate the excess water and methanol to provide short heat residence time and thereby minimize the creation of unwanted side products and/or impurities.

Those having skill in the relevant art will understand that other apparatuses, for example rotary evaporators, horizontal or vertical thin film evaporators and the like, may be utilized to dry the diol product. It is believed that desired results may be obtained when the heat residence time is minimized. Those having skill in the art will appreciate that other separation apparatuses and methods may be utilized to achieve the desired diol composition.

EXAMPLE 8

Non-Commercial Formalin

In certain exemplary embodiments, the source of formaldehyde for the diol production reaction includes freshly prepared formalin (made from para form and water) without the methanol stabilizer present in the commercial formalin. The "wet diol" includes about 27% water, but is substantially free of methanol. Other freshly-prepared formalin examples varied water and methanol content. Diol products formed by reacting these non-commercial formalin cases were dried, as set forth in the examples above, and subject to subsequent thermolysis operations.

Those having skill in the art will appreciate that the diol production, the optional cation-exchange process and the optional drying process may occur in discrete stages with diol product being collected and stored for further processing. In other exemplary embodiments, one or more of the diol production stages are in flow communication such that the output from one stage may be immediately fed to the input of a subsequent stage. In addition, the diol product from any of the diol production stages may be in flow communication with the diol thermolysis reactor, as will be described in greater detail below.

II. Diol Thermolysis

Figure 4:
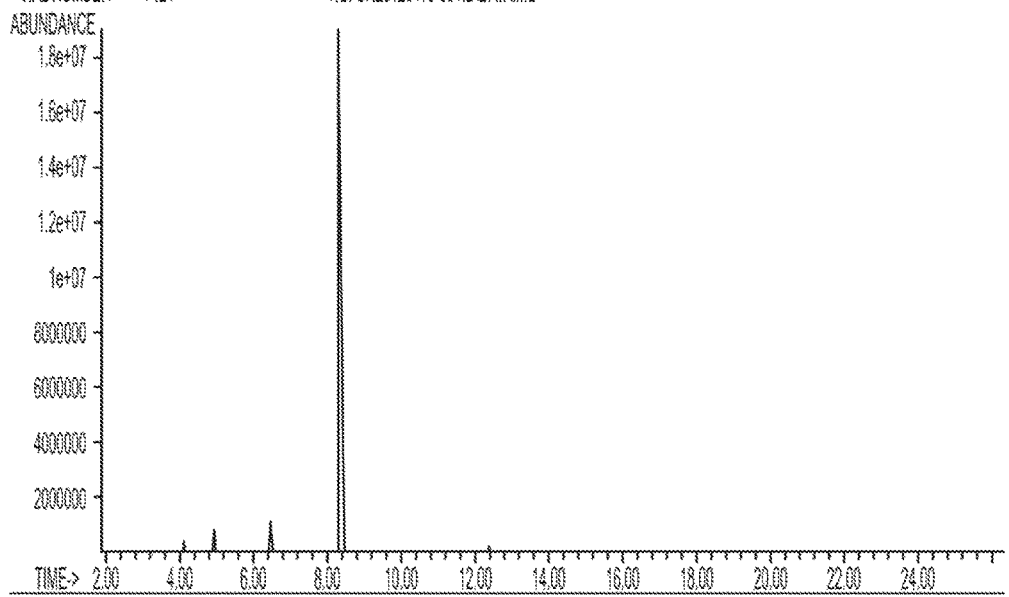
FIG. 4 depicts GC/MS of diethyl bis(hydroxymethyl) malonate starting material with internal standard and 6.5 minute mass spectra.
Figure 4:
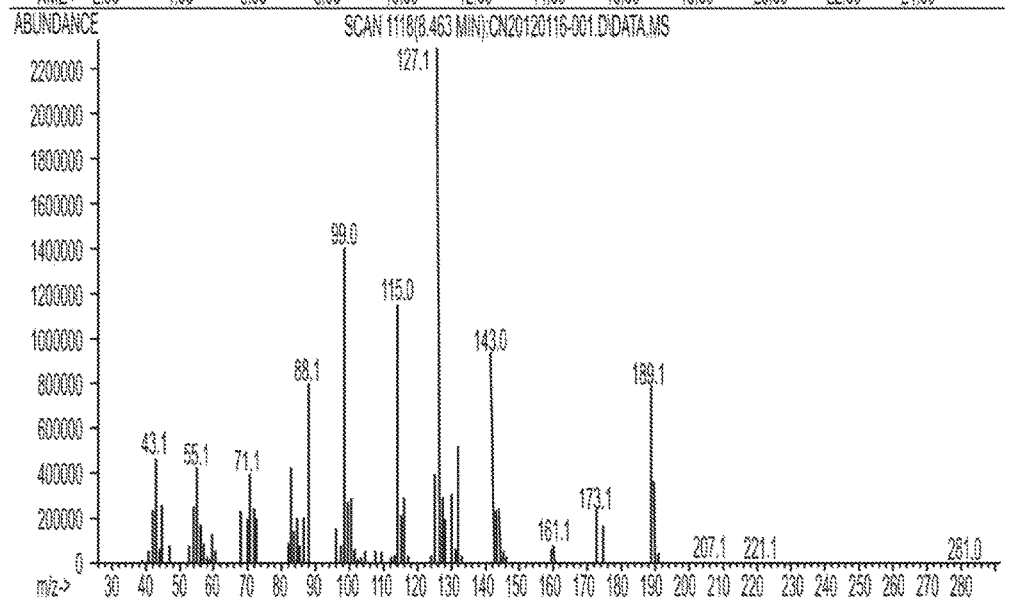
Figure 5:
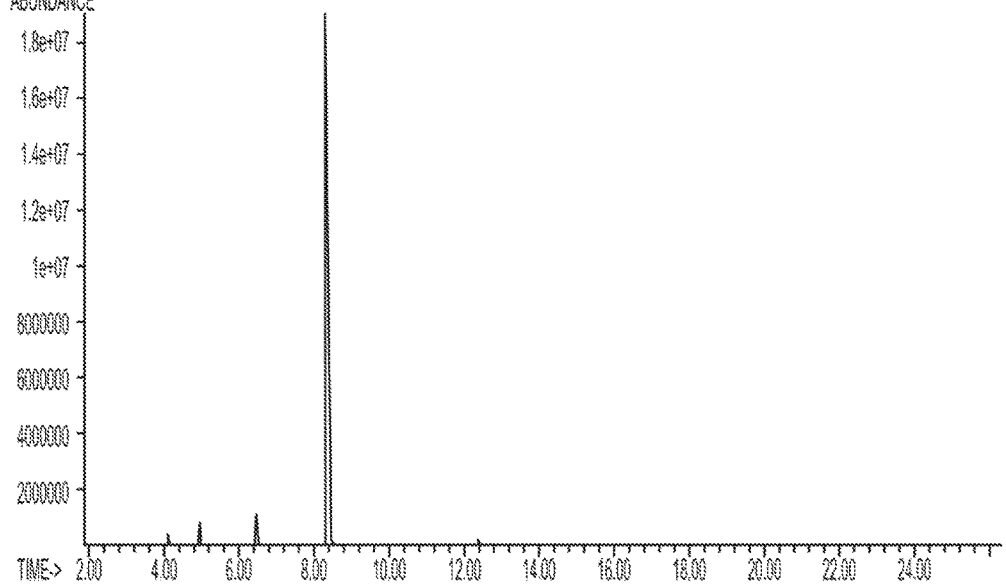
FIG. 5 depicts GC/MS of diethyl bis(hydroxymethyl) malonate starting material with internal standard and 8.4 minute mass spectra.
Figure 5:
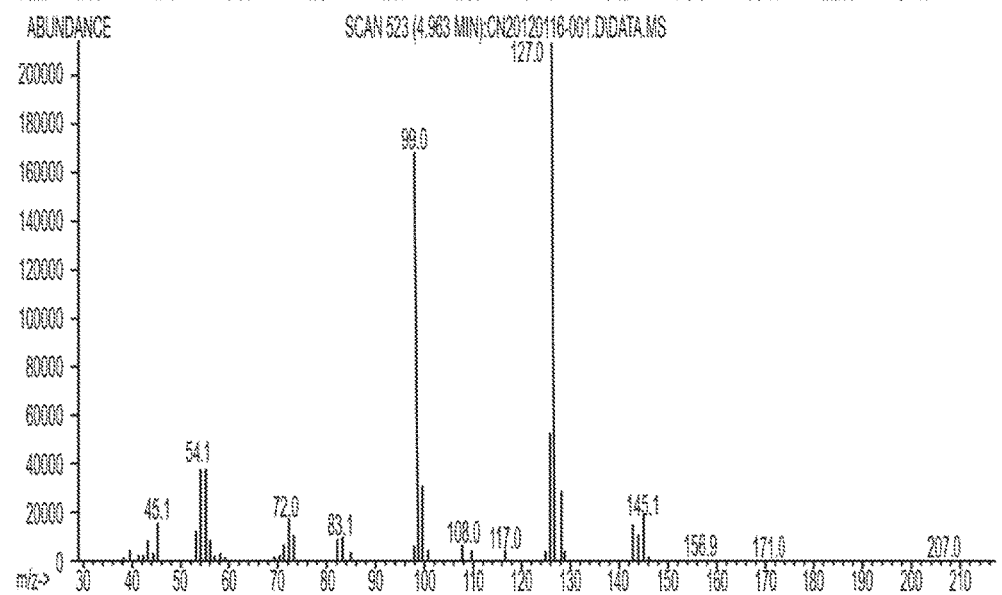
Figure 6:
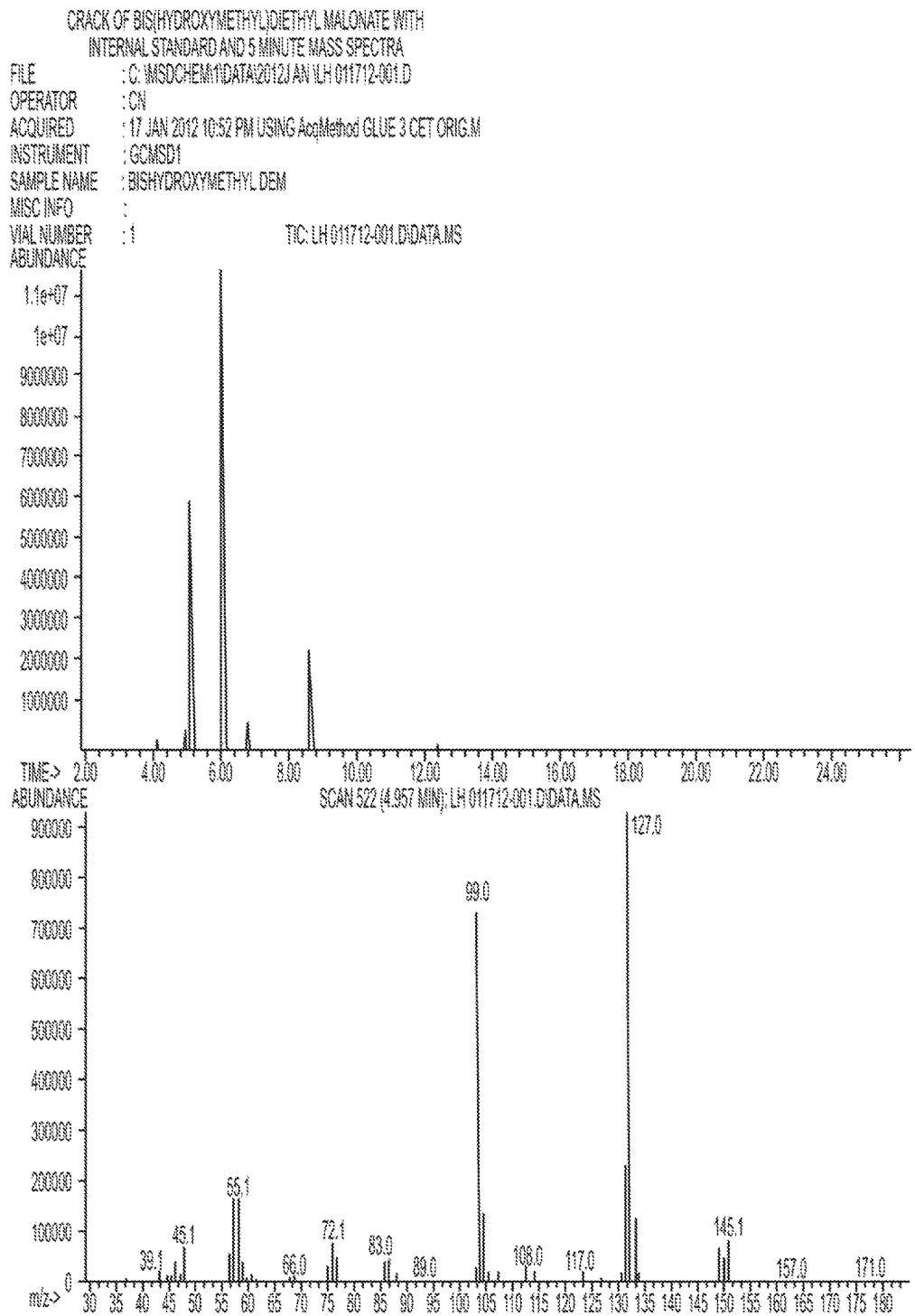
FIG. 6 depicts GC/MS of the cracked material obtained from the diethyl bis(hydroxymethyl) malonate starting material with internal standard and 5 minute mass spectra.

It was observed that during a Knoevenagel reaction using paraform and DEM (as described in the above-mentioned patent applications WO 2012/054616 Synthesis of Methylene Malonates Substantially Free of Impurities, and WO 2012/054633 Synthesis of Methylene Malonates Using Rapid Recovery in the Presence of a Heat Transfer Agent), a significant amount of material was noted in the GC trace at 8.4 minutes. It was postulated that the peak was due to the presence of diethyl bis(hydroxymethyl) malonate in the reaction product (oligomeric species). In order to confirm the speculation, a sample of commercially available diethyl bis(hydroxymethyl) malonate was dissolved in ethyl acetate and a GC/MS was obtained. The GC trace of the commercial product indicated that a small amount of diethyl methylene malonate (DEMM) was formed in the GC itself. See FIGS. 4 and 5. Thereafter, a laboratory attempt was made to crack a small sample (15 g) of the commercial diethyl bis(hydroxymethyl) malonate at 230° C. under vacuum (100 mm Hg). The material to be subjected to thermolysis is a solid and melts at 49-51° C. A heat gun was used to melt the sample and to ensure that it stayed in the liquid state during the crack. Healing tape or a jacketed addition funnel can also be used. The reaction product yielded 10.6 g of cracked material, of which 33 wt % was determined to he DEMM. Thus, this experiment confirmed that DEMM could be obtained through thermolysis of the bis(hydroxymethyl) malonate. See FIG. 6. This experiment was conducted as a batch process. Efforts were then undertaken to produce a scalable, continuous process for diol thermolysis.

EXAMPLE 9

Lab Scale Tube Reactor for Thermolysis Operation

In an exemplary embodiment, a continuous thermolysis operation includes a tube reactor having a packed catalyst in the form of a 12×1½ inch column. The exemplary catalyst is a zeolite commercially available as ZSM-5. The column temperature is maintained at a temperature from about 180 C-200 C. A hot y-adapter at the end of the column provides a first separation of the reaction products. The less volatile material falls out (e.g., unreacted diol, heavies) and the more volatile species (e.g., DEMM, DEM, other lights) are carried to a hot condenser for further separation of reaction products. The hot condenser serves to separate more volatile species from the desired monomer species. The product stream also carries compounds having similar boiling points and other impurities. This product stream is then subjected to further purification measures, such as fractional distillation. Those having skill in the art will appreciate that in a continuous process, various reactor designs may be utilized to collect the desired product stream. In this exemplary embodiment, the crude product may be collected and stored for further downstream processing. In other exemplary embodiments, the thermolysis operation may be in continuous flow communication with a monomer purification process.

Figure 8:
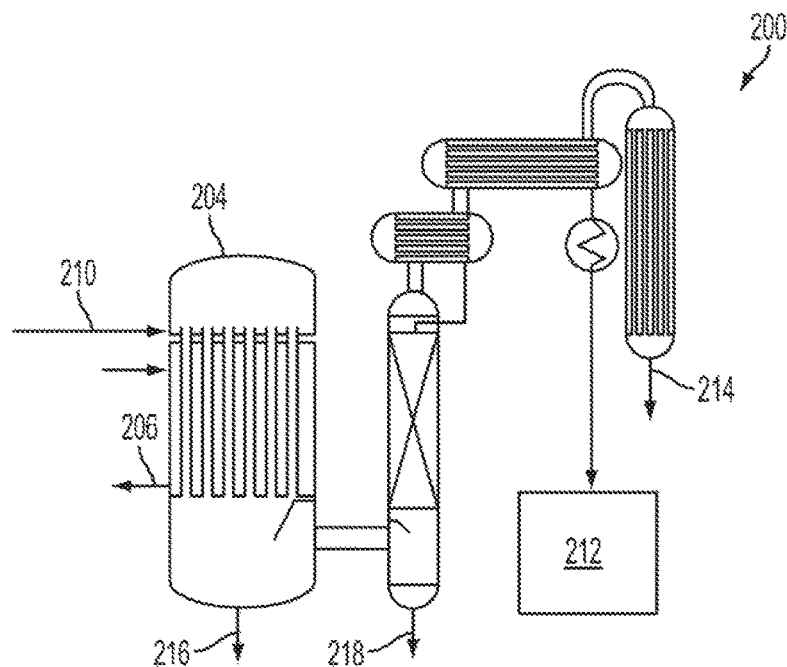
FIG. 8 provides a schematic of a thermolysis reactor and the input and output of the reactor.

In this exemplary embodiment, the diol is preferably pre-heated to about 50-100 C, preferably about 70-85 C. It is beneficial if feed lines are also heated and or insulated to prevent the diol from freezing. In this exemplary embodiment, the thermolysis operation is completed at atmospheric pressure. In this exemplary embodiment, certain polymerization inhibitors may be present during the thermolysis operation to prevent the premature polymerization of the monomer. For example, liquid phase stabilizers (e.g., MSA), vapor phase stabilizers (e.g., TFA), and free-radical stabilizers (e.g., MeHQ) may be used. The patent applications referenced above, and incorporated herein by reference, more fully explain the selection and function of such inhibitors. In certain exemplary embodiments, the inhibitors may be introduced to the thermolysis reactor with the diol. In an exemplary embodiment, an inhibitor package is added to the diol immediately prior to the thermolysis operation. In other exemplary embodiments, an inhibitor package may be added to the crude product collected in the product stream. FIG. 8 illustrates a thermolysis reactor and purification system 200 with the feed and output from the system. Shown are diol feed lines 210 to the thermolysis reactor 204. 206 shows the hot oil outlet line. 212 shows the product collection vessel. 216 shows the heavies output line. 218 shows the output for volatile species. 214 shows output of compounds having similar boiling points and other impurities 214. In certain other exemplary embodiments, an inhibitor package may be added to the crude product prior to any further purification operations.

EXAMPLE 10

Pilot Plant Scale Tube Reactor for Thermolysis Operation

In an exemplary embodiment, the thermolysis operation was performed in a continuous process using a scaled version of the lab reactor of Example 9. In an exemplary embodiment the catalyst column was contained in a reactor tube having a nominal 1.5-inch actual diameter and a height of about 30 inches, holding approximately 400 g of the ZSM-5 zeolite. The reactor is heated using circulating hot oil set to a healing temperature between 200-230 C. The diol heater is set to about 80-90 C, and the diol feed lines are warmed to approximately 50-60 C.

In an exemplary embodiment, the walls of the tube reactor are heated and maintained at approximately 180-250 C. Suitable heat transfer is required to ensure that a desired reaction temperature is maintained in the catalyst column. In an exemplary embodiment, the thermolysis takes place under atmospheric pressure. In other exemplary embodiments, the thermolysis may take place under vacuum conditions or pressurized conditions.

As in the lab scale reactor, the product from the thermolysis reactor is divided into streams using various apparatuses such as knock-down condensers, hot condensers, condensers, and the like. In an exemplary embodiment, the product stream comprising crude monomer species and other close boilers or impurities is collected for further downstream treatment. The downstream treatment may include various distillation or other separation techniques and stages to achieve the desired isolated monomer species.

In an exemplary embodiment, the crude monomer product stream may be in flow communication with the downstream purification operation.

The catalyst column diameter may be ½ in, 1 in., 3 in., 4 in., or any size able to provide the desired reaction temperature. In certain exemplary embodiments, the thermolysis reactor may comprise multiple catalyst columns. In certain exemplary embodiments, the multiple columns may be fed with a single diol feed line. In other exemplary embodiments, the multiple columns may be fed with a plurality of diol feed lines. Those having skill in the art will ascertain that various reactor designs are possible in order to achieve the desired outcome.

It is believed that efficient diol thermolysis takes place when the reaction temperature is between about 180 C and 220 C. In the theoretical reaction, the diol will disassociate or "crack," releasing a mole of formaldehyde and a mole of water for each mole of monomer formed. Optimal reaction conditions are desired such dial unwanted side products are reduced, and monomer yield is maximized. Reaction conditions include temperature, catalyst loading, catalyst shape (e.g., cylinders, beads), inlet diol temperature, feed rate, reaction pressure, and temperature of various apparatuses in the reaction set up (e.g., condensers, collection flasks) as those having skill in the art will readily appreciate.

EXAMPLE 11

Batch Process, Dropwise Addition of Reactant

Figure 2:
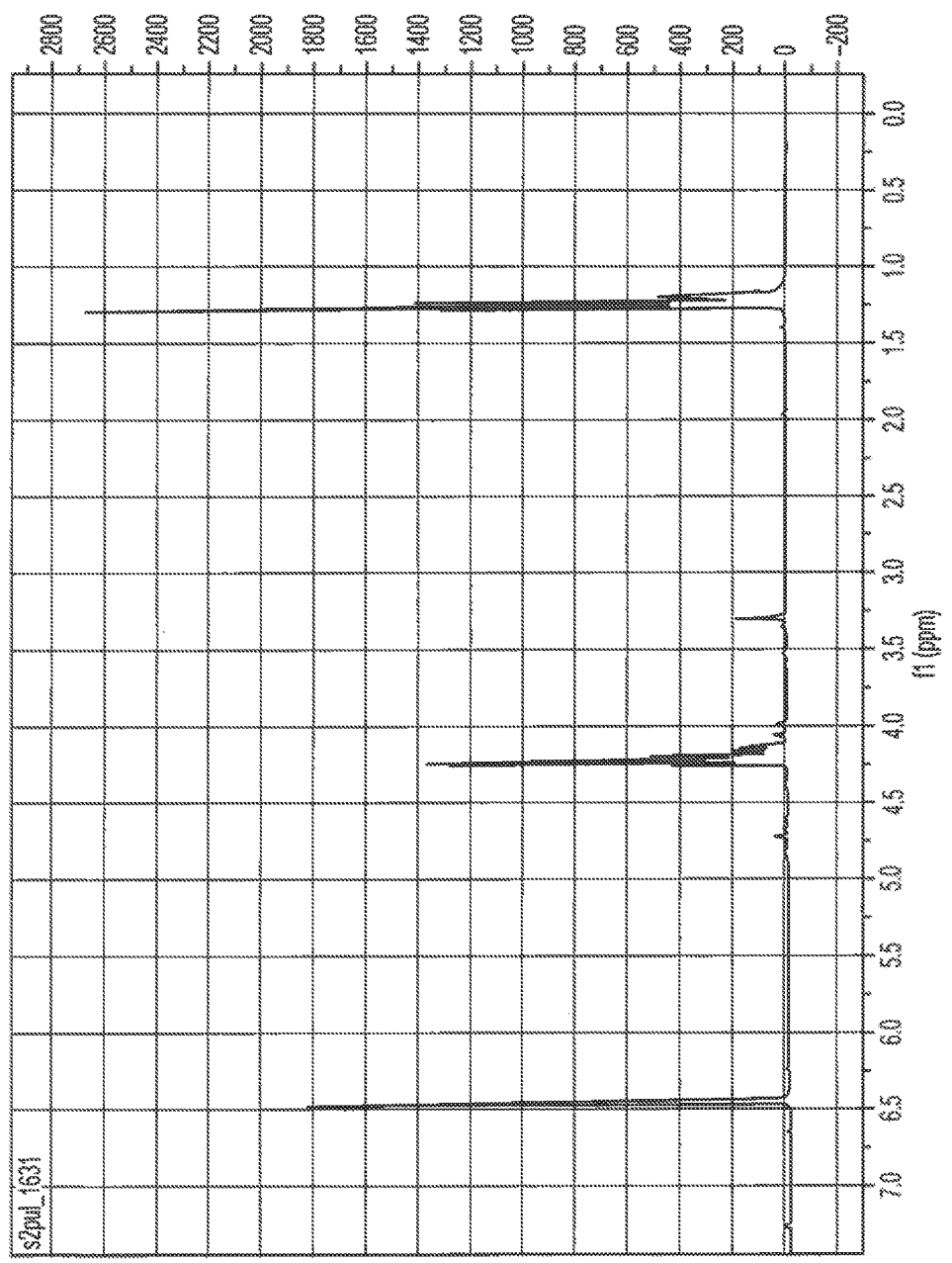
FIG. 2 depicts HNMR showing production of diethyl methylene malonate by thermolysis of diethyl bis(hydroxymethyl) malonate intermediary with drop-wise addition.

Assemble a short path distillation apparatus equipped with 250 mL round bottom flask, addition tunnel, mechanical stirrer, condenser, receiving flask and vacuum. Charge 250 mL round bottom flask with copper zeolite (2 g). Heat contents to 200° C. with oil bath. Apply vacuum (100 mm Hg). Slowly add intermediary diethyl bis(hydroxymethyl) malonate (30 g., 0.136 mol) drop-wise onto the copper zeolite. After completion of this addition, cool apparatus to 25° C. and back fill apparatus with $N_2$. Dry distillate over anhydrous $Na_2SO_4$ (1 g). The desired reaction product is diethyl methylene malonate (DEMM). In an exemplary embodiment, the yield is 20.5 g (88%). See FIG. 2.

EXAMPLE 12

Batch Process, One-Pot Method

Figure 3:
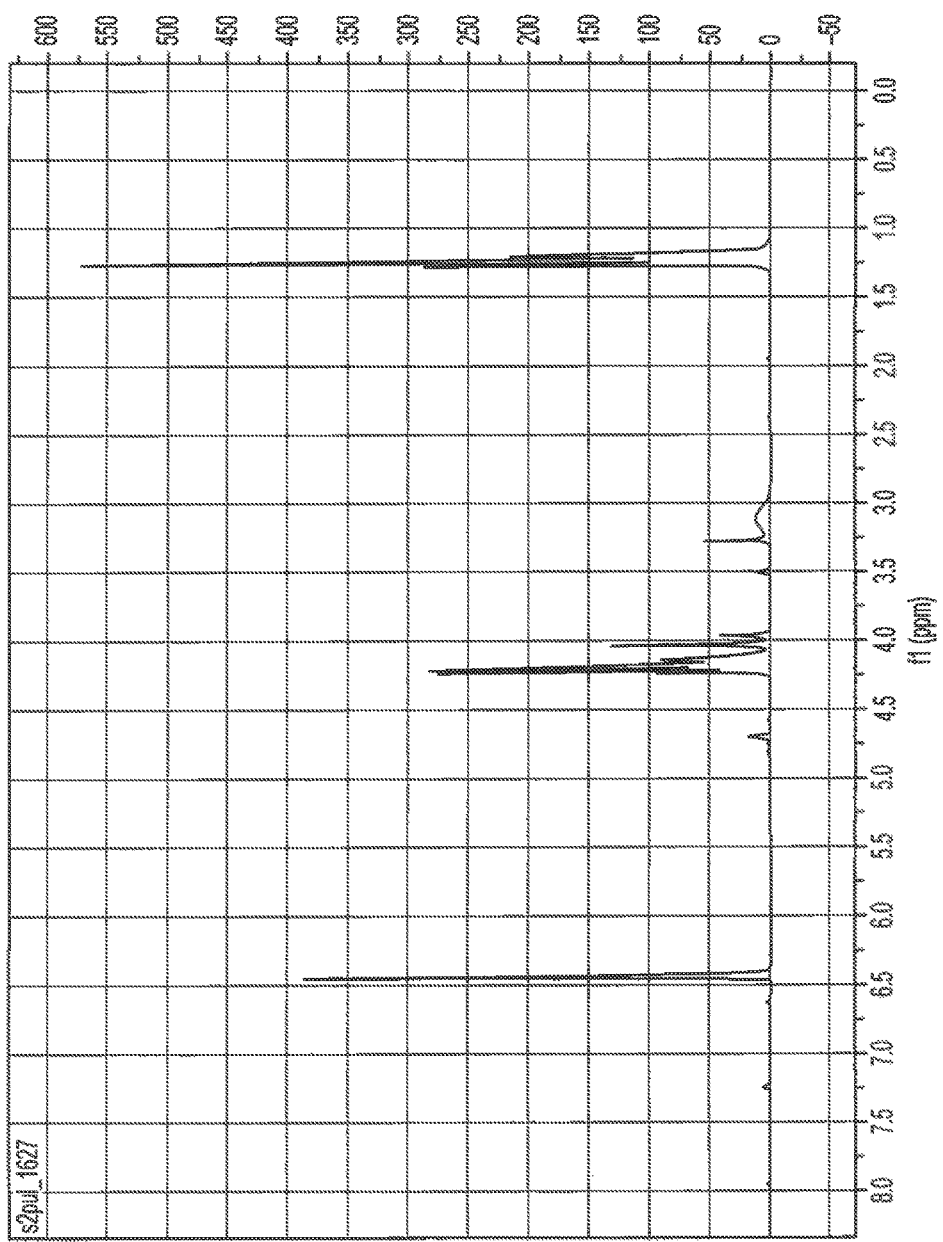
FIG. 3 depicts HNMR showing production of diethyl methylene malonate by thermolysis of diethyl bis(hydroxymethyl) malonate intermediary in a batch process.

Assemble a short path distillation apparatus equipped with 250 mL round bottom flask, mechanical stirrer, condenser, receiving flask and vacuum. Charge 250 mL round bottom flask with copper zeolite (2 g) and diethyl bis (hydroxymethyl) malonate (30g. 0.136 mol). Apply vacuum (100 mm Hg). Heat contents to 200° C. with an oil bath. An oil bath was pre-heated to 200° C. prior to lowering the reaction flask into the oil bath. After completion thermolysis, cool apparatus to 25° C. and back fill apparatus with $N_2$. Dry distillate over anhydrous $Na_2SO_4$ (1 g). The desired reaction product is DEMM. In an exemplary embodiment, the yield is 19 g (81%). See FIG. 3.

EXAMPLE 13

Thermolysis of Commercial Diol

In an exemplary embodiment, commercially available diethyl bis(hydroxymethyl) malonate was utilized lather than synthesizing diol in the lab from DEM. The diethyl bis(hydroxymethyl) malonate was subjected to certain thermolysis processes disclosed herein, and the reaction product was purified to yield the desired monomer species. In other exemplary embodiments, commercially available diols of other dialkyl malonates were subjected to thermolysis in accordance with certain of the processes disclosed herein to obtain a desired monomer species. In other exemplary embodiments, diols of other dialkyl malonates were first synthesized, then subjected to certain of the thermolysis processes disclosed herein, to obtain a desired monomer species.

EXAMPLE 14

Catalyst Slurry

In yet another exemplary embodiment, a suitable catalyst may be carried in a diol slurry and contacted with a hot surface or otherwise exposed to sufficient heat to effect the diol thermolysis reaction.

III. Product Clean-Up

The reaction product from the thermolysis operation may be purified by various methods. In an exemplary embodiment, a variety of separation techniques are employed. For example, a series of condensation and/or distillation steps may be utilized to separate the desired monomer species from impurities and side reaction products. In exemplary embodiments, hot condensers, condensers, vacuum distillation apparatuses, simple distillation apparatuses and/or fractional distillation apparatuses may be utilized. In some exemplary embodiments, the separation techniques may be employed at atmospheric pressure, under vacuum, or under elevated pressure in accordance with sound engineering principles. Likewise, the separation techniques may be employed at ambient temperature, at reduced temperatures or at elevated temperatures, in accordance with sound engineering principles.

IV. Plant Design: Modular Units

Exemplary embodiments of the invention include a plant for producing a methylene malonate monomer, the plant may be designed with modular units wherein one or more modular units are diol production units, diol purification units, monomer production units, monomer purification units, or a combinations thereof. Each unit may be self-contained for the desired processes associated therewith. Alternately, one or more of the modular units may be in flow communication such that the outlet from one process is fed to the inlet of another process in a continuous manner.

An exemplary plant includes at least one diol production unit, at least one diol purification unit, and at least one monomer production unit.

Another exemplary plant includes at least one diol production unit, at least one diol purification unit, at least one monomer production unit, and at least one monomer purification unit.

Another exemplary plant includes at least one monomer production unit, and at least one monomer purification unit.

Another exemplary plant includes at least one diol production unit, optionally, at least one diol purification unit, at least one monomer production unit, and optionally, at least one monomer purification unit.

The exemplary diol production unit comprises a diol reactor apparatus capable of reading a dialkyl malonate ester and a source of formaldehyde in the presence of a reaction catalyst.

The exemplary diol purification unit comprises an ion-exchange column and a separation apparatus, such as a wiped-film evaporator, a rotary evaporator, or a vertical or horizontal thin-film evaporator.

The exemplary monomer production unit comprises at least one catalyst column and a heating apparatus for maintaining the temperature of the at least one catalyst column.

Another exemplary monomer production unit comprises a plurality of catalyst columns and at least one heating apparatus for maintaining the temperature of the plurality of catalyst columns.

Equivalents

Those skilled in the art will recognize, or be able to ascertain using no more than routine experimentation, many equivalents to the specific embodiments of the invention described herein. Such equivalents are intended to be encompassed by this invention.

What we claim is:

1. A plant for producing a methylene malonate monomer comprising:
    at least one diol production unit comprising a diol reactor apparatus capable of reacting a dialkyl malonate ester and a source of formaldehyde in the presence of a catalyst,
    at least one diol purification unit,
    at least one monomer production unit comprising a plurality of catalyst columns and at least one heating apparatus for maintaining the temperature of the plurality of catalyst columns, and at least one monomer purification unit comprising a condensation apparatus, a fractional distillation apparatus, or both;
    wherein the at least one diol production unit is in communication with the at least one diol purification unit, and the at least one diol purification unit is in communication with the at least one monomer production unit, and the at least one monomer production unit is in communication with the at least one monomer purification unit.

2. The plant according to claim 1 wherein the at least one monomer production unit comprises at least a single reactant feed line to feed the plurality of catalyst columns.

3. The plant according to claim 1 wherein the short heat residence apparatus comprises a wiped-film evaporator, a rotary evaporator, a horizontal thin-film evaporator or a vertical thin-film evaporator.

4. The plant according to claim 1 wherein the short heat residence apparatus comprises a wiped-film evaporator.

5. The plant according to claim 1 wherein the at least one diol production unit is a continuous flow reactor.

6. The plant according to claim 5 wherein the at least one diol production unit comprises a shell having a plurality of static mixers and reactant inlets.

7. The plant according to claim 5 wherein the at least one diol production unit comprises an inlet to add a pH lowering agent.

8. The plant according to claim 5 wherein the at least one diol production unit is maintained in a medium to control reaction temperature.

9. The plant according to claim 8 wherein the medium to control reaction temperature is a water bath.

10. The plant according to claim 1 wherein the at least one monomer production unit which comprises a plurality of catalyst columns packed with ZSM catalyst.

11. The plant according to claim 1 wherein the diol purification unit communicates with the monomer production unit through feed lines wherein the feed lines are heated.

12. The plant according to claim 11 wherein the at least one heating apparatus is a heat transfer system.

13. The plant according to claim 1 wherein the heat transfer system uses hot oil to heat the plurality of catalyst columns.

14. The plant according to claim 1 wherein the at least one monomer production unit comprises an output line for heavies, an output line for volatile species.

15. The plant according to claim 1 wherein the at least one monomer production unit comprises a plurality of catalyst columns having a diameter of about 0.5 to about 4.0 inches and a length of about 12 to about 72 inches.

16. The plant according to claim 1 wherein:
    the at least one diol purification unit is capable of purifying bis(hydroxymethyl) malonate,
    the at least one monomer production unit is capable or reacting bis(hydroxymethyl) malonate with a catalyst to form a methylene malonate monomer, and
    the at least one monomer purification unit is capable of isolating methylene malonate monomer.

* * * * *